United States Patent [19]

Scharf et al.

[11] 3,992,294

[45] Nov. 16, 1976

[54] PROCESS FOR SEQUESTERING METAL IONS

[75] Inventors: Daniel J. Scharf, Cheektowaga; Howard A. Chamberlin, Grand Island, both of N.Y.

[73] Assignee: Hooker Chemicals & Plastics Corporation, Niagara Falls, N.Y.

[22] Filed: Jan. 7, 1974

[21] Appl. No.: 431,194

[52] U.S. Cl. .................................. 210/58; 252/180
[51] Int. Cl.² ................................ C02B 5/06
[58] Field of Search ............... 210/58, 59; 260/502.4 R, 502.4 A, 502.4 P, 938; 252/180, 181

[56] References Cited
UNITED STATES PATENTS

| | | | |
|---|---|---|---|
| 3,336,221 | 8/1967 | Ralston | 210/58 X |
| 3,434,969 | 3/1969 | Ralston | 210/58 |
| 3,763,281 | 10/1973 | Weil | 260/938 |

FOREIGN PATENTS OR APPLICATIONS

| | | | |
|---|---|---|---|
| 47-112 | 1/1972 | Japan | 260/938 |

*Primary Examiner*—Thomas G. Wyse
*Attorney, Agent, or Firm*—Peter F. Casella; William J. Crossetta, Jr.

[57] ABSTRACT

A process is disclosed for sequestering metal ions by treating said ions with a compound of the formula:

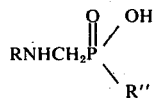

wherein R' is selected from the group consisting of ⁻OH, alkyloxy and aryloxy; and R is selected from the group consisting of

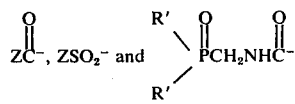

wherein Z is ⁻OH, alkyl, aryl, alkoxy and aryloxy.

17 Claims, No Drawings

PROCESS FOR SEQUESTERING METAL IONS

BACKGROUND OF THE INVENTION

The use of complexing agents which combine with metal ions in solution to form soluble complexes (which agents are commonly referred to as sequestrants) is of great importance in many industrial processes inasmuch as it may prevent undesired precipitation reactions from occurring. For example, sequestration of calcium is important in water treatment and in laundry solutions for controlling hardness of the water. Sequestration of the heavy metals such as copper and nickel is essential in such areas as textile processing, metal cleaning and finishing. Not all sequestrants, however, are equally effective, their activity varying with their structures and the conditions under which they are used, for example, the common carboxylic acid sequestrants are often ineffective in preventing ferric ion precipitation from alkaline solutions of pH greater than 8.

The commercial utilization of water-soluble chelating compounds in agricultural applications to provide trace elements for plant growth is well known. Likewise, the treatment of plants suffering from chlorosis as a result of growth in alkaline soils devoid of sufficient assimilatable iron is known. Various chelating agents have been employed in the past to correct iron deficiencies in plants, the water solubility of chelated metal ions affords a primary route for potential assimilation into a plant structure.

Ethylenediaminetetraacetic acid (EDTA) has been employed in the past for treatment of iron deficiencies of citrus trees under acid conditions. The EDTA iron chelates are not stable in neutral and alkaline media. The development of sequestrants which may be employed in acid media as wel as alkaline media is significant not only for agricultural applications, but for use in the detergent field, metal cleaning field, textile and dye industry and as stabilizers for organic and inorganic peroxides.

The use of the sequestrants in sulfite baths for the electrodeposition of gold and gold alloys as additives for improving the performances and the operating conditions of said baths is also of high importance. In general, additives which will strongly limit, during electrolysis, the influence on the quality of the deposits of the variations of some operating factors, such as temperature, pH of the bath, current density, type and degree of agitation, etc., are desirable. It is well known in the art of electrodepositing gold and gold alloys from sulfite baths that the above operating factors normally have a strong influence on the nature and the properties of the coatings obtained. Thus, it is often necessary to accurately control some of said factors in order to obtain deposits having the properties required (color, ductility, gloss, etc.). Most often, relatively slight variations of current density result in the formation of foggy deposits, burns, pittings or color changes, particularly when depositing gold alloys. The introduction of the instant compounds into sulfite gold baths largely prevents these difficulties. In the presence of such additives, it is possible to vary operational factors between relatively wide limits without affecting the quality of the coatings and, in the case of gold alloys, without appreciably modifying the composition and the carat thereof. The principle of action of these additives is not known exactly; it is, however, possible that they may standardize the electrochemical properties of the various metals which are plated simultaneously, e.g., the electrodeposition potential and the distribution of ions in the cathode layer.

Further, many flame retarding agents and methods of application have been developed in attempts to obtain flame resistant textile materials and thermoplastic resin compositions.

Flame retardant textiles have been produced by depositing metal oxides, within or on the textile fibers, by the successive precipitation of ferric oxides and a mixture of tungstic acid and stannic oxide or by successive deposition of antimony trioxide and titanium dioxide. Such processes require plural treatment baths in which strongly acidic solutions are employed, thus posing the problem of possible textile degradation. Furthermore, metal oxide coatings on textile materials create difficulties in subsequent dyeing processes which deleteriously affect the hand of the finished product. Other processes involve the use of a single processing bath wherein a dispersion of chlorinated hydrocarbon and finely divided antimony oxide is padded on the textile material. Near the textile combustion temperature, antimony oxide will react with hydrogen chloride, generated by degradation of the chlorinated hydrocarbon, to form antimony oxychloride which acts to suppress flame. This combination of a chlorinated hydrocarbon and finely divided antimony oxide are not acceptable finishes for closely woven textiles as they deleteriously affect the hand of the finished product. A further process for imparting flame resistance to cellulosic materials is by the esterification of the cellulose with diammonium hydrogen ortho-phosphate. Textile products so treated, however, are subjected to metathesis reaction with cations during washing, and must be regenerated by reacting the wash product with an ammonium chloride solution.

The production of thermoplastic resin compositions which are flame retardant is of considerable commercial importance. For example, such articles as castings, moldings, foamed or laminated structures and the like are required, or are at least desired, to be resistant to fire and flame and to possess the ability to endure heat without deterioration. The use of various materials incorporated into thermoplastic resins so as to improve the flame retardancy thereof has been known. Many compounds have been commercially available for such use, among them being chlorostyrene copolymers, chlorinated paraffin wax in admixture with triphenyl styrene, chlorinated paraffins and aliphatic antimonical compounds, as well as antimony oxide-chlorinated hydrocarbon mixtures. A problem associated with these compounds has been, however, the fact that generally a large amount, i.e., upwards to 35% of additive, must be incorporated into the resin in order to make it sufficiently flame retardant. Such large amounts of additive may deleteriously affect the physical characteristics of the thermoplastic resin, as well as substantially complicating and increasing the cost of preparation thereof. A further problem is that these prior art additives tend to crystallize or oil out of the resin after a relatively short time of incorporation. The present invention relates to a group of compounds which may be added to thermoplastic resins in relatively small amounts and still produce satisfactory flame retardant compositions which will not crystallize nor oil out of the resin after incorporation therein.

OBJECTS OF THE INVENTION

It is, therefore, a principal object of this invention to provide novel compounds of the formula:

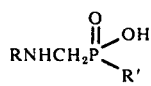

wherein R' is selected from the group consisting of ⁻OH, alkoxy and aryloxy; and R is selected from the group consisting of:

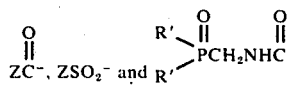

wherein Z is ⁻OH, alkyl, aryl, alkoxy and aryloxy; provided when R' is

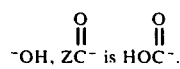

Another object is to provide a method for treating normally flammable cellulosic, proteinaceous or analogous man-made materials to render them flame retardant. Another object is to produce a flame retardant additive which chemically combines with the material being treated. Another object is to provide flame retarding thermoplastic resin compositions comprising normally flammable thermoplastic resin materials. A further object is to provide a process for treating normally flammable thermoplastic resin compositions to render them flame retardant. A particular object is to devise a composition comprising normally flammable cellulosic, proteinaceous or analogous man-made materials and an effective flame retardant amount of the compound represented by the formula:

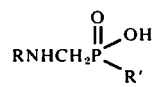

wherein R and R' are as above described. Furthermore, in accordance with the instant invention, there is provided a process for sequestering metal ions from aqueous solution by reacting the sequestrant mixture of this invention with metal ions. Also, this invention provides novel compositions of matter comprising the sequestered metal ion derivatives of the sequestrant mixtures of this invention. Still furthermore, an object of this invention is to provide an additive useful in improving the electrodeposition of precious metals in electrochemical deposition process.

These and other objects of the present invention will be obvious from the following description.

SUMMARY OF THE INVENTION

It has been discovered that certain compounds have unexpected utility as flame retardant additives and metal ion sequestrants. In accordance therewith, the instant invention relates to compounds of the formula:

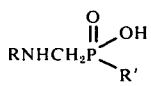

wherein R' is selected from the group consisting of ⁻OH, alkoxy, preferably of 1–6 carbon atoms, and aryloxy, and R is selected from the group consisting of:

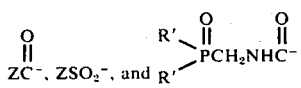

wherein Z is selected from the group consisting of ⁻OH, alkyl and alkoxy, preferably of 1–6 carbon atoms, aryl and aryloxy, and their use as metal ion sequestrants and flame retardant additives.

Illustrative examples of compounds of the present invention include, for instance, compounds of the structure:

 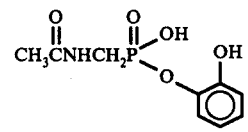

 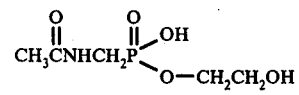

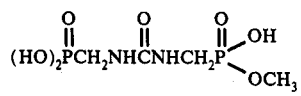 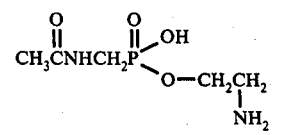

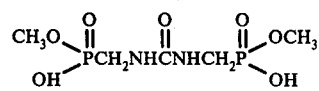 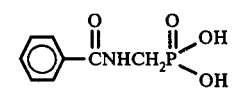

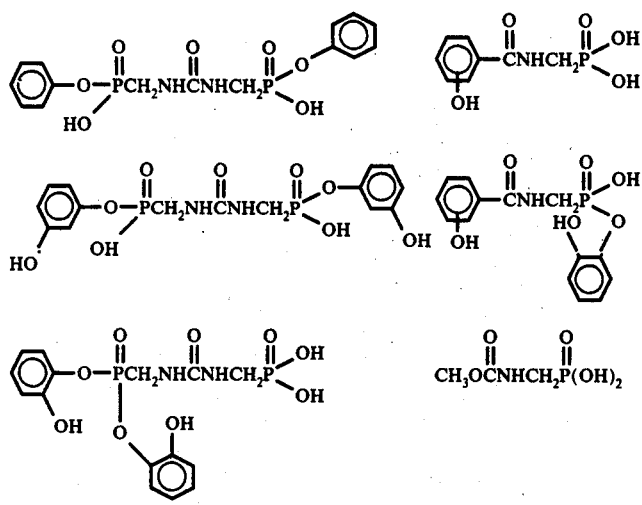
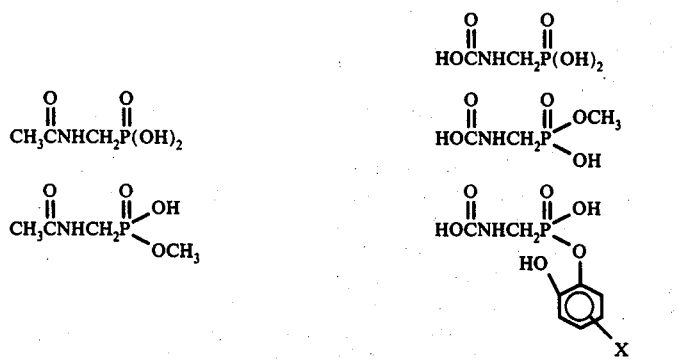
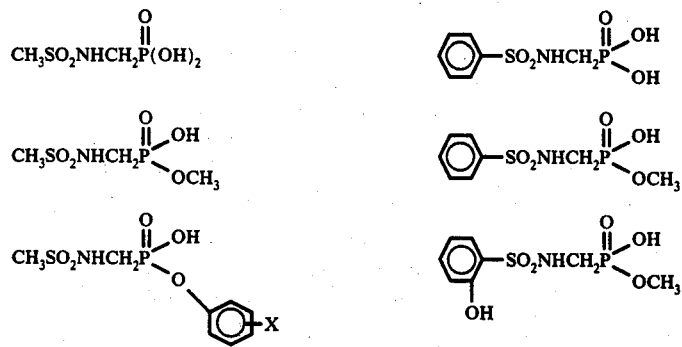
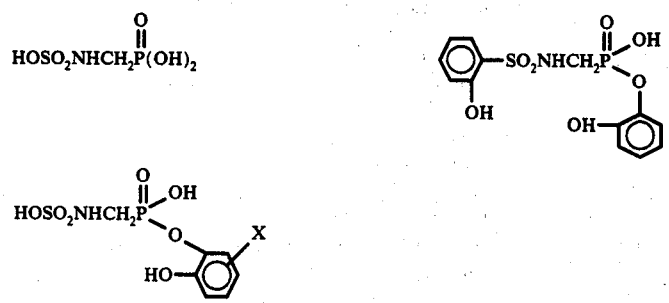
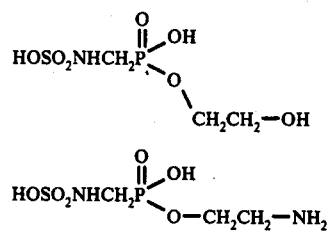

The synthesis of the compounds of the instant invention may be accomplished by various processes. Compounds of the type:

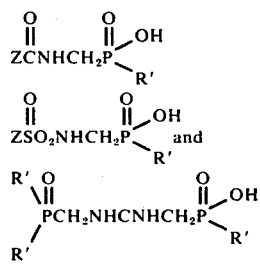

wherein Z and R' are as previously described, may be prepared by reacting corresponding N-hydroxy methyl amides, N-hydroxy methyl sulfonamides and methylolated ureas of the formulae:

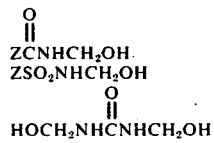

wherein Z is as previously described, providing it is not OH⁻, with a stoichiometric or excess amount of trialkyl phosphite in a suitable solvent, or neat, to form intermediate compounds of the formulae:

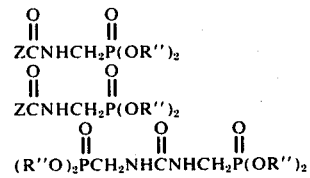

wherein R'' is alkyl. Typically, the reaction occurs at elevated temperatures and is continued for about 1 to about 12 hours. Temperatures are generally from about 50° C to about 160° C. Preferably, the reaction is continued from about 3 to about 6 hours at a temperature of about 80° C to about 120° C. The solvent or other volatile matter is, thereafter, stripped or otherwise removed from the product. Suitable solvents include benzene, toluene, xylene, glymes, N-N-dimethyl formamide, and aliphatics or aromatic hydrocarbons. Alternately, the corresponding N-hydroxy methyl amide, N-hydroxy methyl sulfonamide and methylolated urea starting materials may be reacted with a phosphorus trihalide by the method of U.S. Pat. No. 2,304,156 to form the dihalogenated, phosphonate or diphosphonate intermediate. The dialkyl phosphonate or dihalogenated phosphonate intermediate may then be selectively hydrolyzed to provide the final compounds.

Typical compounds suitable as reactants herein include:

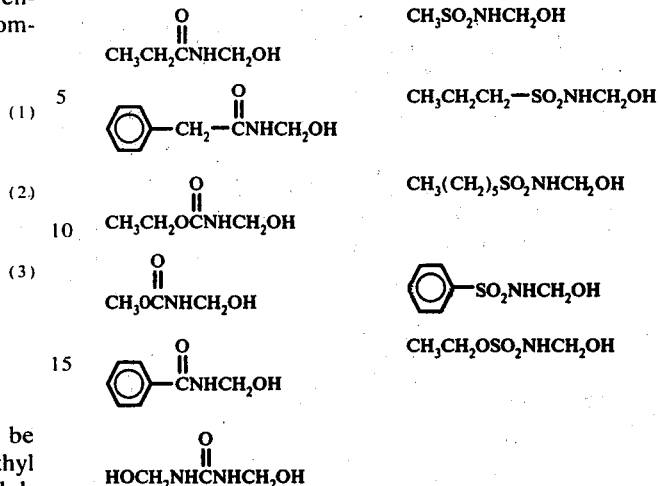

The metal ions which may be sequestered by the composition of this invention are those cations having a valence of two or more, such as the ions of calcium, chromium, copper, nickel, tin, aluminum, cobalt, platinum, palladium, rhodium, iridium, ruthenium, osmium, zirconium, hafnium, the rare earths such as gadolinium, europium, neodymium, the actinides such as uranium, and iron.

The compounds of this invention, when added to those solutions in which sequestration is desired, may be added as a solid or as a solution. If it is desired to add said compounds as a solution, the compound may be dissolved in water. From about 0.001 percent to about 50 percent concentration (by weight) may be used, though it is preferred to use from about 0.01 to about 5 percent concentration (by weight), and it is even more preferred to use from about 0.1 to about 3 percent concentration (by weight).

It is preferred to use said compounds as sequestrants in aqueous solutions. When said composition is added to the solution containing metal ions to be sequestered, the temperature of said solution may be from about 0° to about 100° centigrade, though it is preferred that said temperature be from about 20° to about 70° centigrade, and it is even more preferred that said solution be at ambient temperature.

The compounds of this invention are preferably used as additives in sulfite baths for the electrodeposition of gold and gold alloys. They can comprise one or more phosphorus atoms and the acid functions thereof can be free, esterified partially or completely. It has been found that in many cases the esters are as active or more active than the corresponding free acids when added to gold baths and this observation is very surprising and completely unexpected. Indeed, if, as it is generally supposed, the activity of the free acid additives is due to the affinity between the acid OH functions and the metal ions dissolved in the bath, it is difficult to understand how the ester functions which should be relatively inert can even be more active. It should also be noted that the carbonyl derivatives of the present organo-phosphorus compounds are particularly active.

The effective quantities of the compounds useful according to the invention can vary between wide limits. These quantities depend, naturally, on the chemical structure of the phosphorus compound considered, that is on the nature and the number of the functional groups and, presumably, on their orientation. In some cases, a few mg/l, e.g. 1 to 2 mg/l are sufficient; in other cases higher concentrations, e.g., of the order of 10 to 100 g/l or even up to the limit of solubility in the bath can be desirable and advantageous.

One or more of the novel compounds of this invention may be applied to textile materials by conventional finishing techniques such as by thermal induced pad curing so as to incorporate into the textile a flame retardant amount thereof. The compounds of this invention have advantages over the flame retardant agents of the prior art in that they may be used on a variety of textile materials of different chemical composition, and they may be applied by a variety of methods. They may be applied to materials in either the fiber or fabric form to give flame retarding materials with minimum detectable physical changes in the quality or hand of the textile material.

Products of this invention may be applied to cellulosic materials in several ways to give a durable flame retardant treatment. Aqueous mixtures of the products with formaldehyde, urea, trimethylol melamine or other known cellulose crosslinking agents may be applied to cellulose substrates with or without the aid of an acidic catalyst by a padding process. The cellulosic material may be immersed in an aqueous solution of the compounds, trimethylol melamine, and $Zn(NO_3)_2 \cdot 6H_2O$ and squeezed on a two roll padder to 70–90% wet weight pick-up. The material is dried at 220°–270° for 1–3 minutes and cured at 300°–370° F for 1–6 minutes in a circulating air oven. The samples are then washed in hot water and dried. The finished samples have a flame retardant add-on of about 5 to about 40% and preferably about 10 to about 25% by weight.

The flame retardant agents of this invention may be applied to various textiles such as cellulosic materials, proteinaceous materials and blends of cellulosic or proteinaceous materials with analogous man-made fibers. By cellulosic materials, applicant intends to embrace cotton, rayon, paper, regenerated cellulose and cellulose derivatives which retain a cellulose backbone of at least one hydroxy substituent per repeating glucose unit. By proteinaceous material applicant intends to embrace those textile materials comprising the functional groups of proteins such as the various animal wools, hairs and furs.

The flame retardant compounds or additives of the invention may be incorporated into resin compositions by known methods. That is, to say, the flame retardant additive may be added to the resin by milling the resin and the additive on, for example, a two-roll mill, or in a Banbury mixer, etc., or it may be added by molding or extruding the additive and resin simultaneously, or by merely blending it with the resin in powder form and thereafter forming the desired article. Additionally, the flame retardant may be added during the resin manufacture, i.e., during the polymerization procedure by which the resin is made, provided the catalysts, etc., and other ingredients of the polymerization system are inert thereto. Generally, the compounds of this invention may be incorporated into the thermoplastic resin in flame-retarding amounts.

It should be noted that it is also within the scope of the present invention to incorporate such ingredients as plasticizers, dyes, pigments, stabilizers, antioxidants, antistatic agents and the like into the novel composition.

ASTM Test D2863-70, used in accordance with the following examples, generally provides for the comparison of relative flammability of self-supporting plastics by measuring the minimum concentration of oxygen in a slowly rising mixture of oxygen and nitrogen that will support combustion. The procedure encompasses supporting cylindrical test specimens 70–200 × 8.0 mm. vertically in a glass tube fitted with controlled upward oxygen/nitrogen gas flow. The top of the specimen is ignited and oxygen flow is adjusted until it reaches that minimum rate at which the specimen is extinguished before burning 3 minutes or 50 mm. whichever happens first. The oxygen index(n) is then calculated as follows:

$$n,\% = (100 \times O_2)/(O_2 + N_2)$$

wherein $O_2$ is the volumetric flow of oxygen, at the minimal rate and $N_2$ is the corresponding volumetric flow rate of nitrogen.

AATCC test method 34-1969, The Vertical Char Test, used in accordance with the following examples, generally provides for the comparison of relative flammability of 2 ¾ inch × 10 inch fabric test specimens when exposed to a controlled burner flame, under controlled conditions, for periods of 12.0 and 3.0 seconds. Charred specimens are thereafter subjected to controlled tearing tests, using tabulated weights, to determine the average tear length as representing the char length of the fabric. In addition, samples which are wholly consumed by the flame are rated (B) and samples which do not burn are rated (NB). For comparison purposes, it should be noted that untreated samples of the fabrics used in the examples of this case would be consumed by this test.

In all the examples of the application, the following general procedure was used except when otherwise specifically noted. Padding was done on a standard two roll laboratory padder at a gauge pressure of about 60 pounds per square inch in all cases. Drying and curing during processing were done with a standard laboratory textile circulating air oven. Washing and drying was done in a standard, home, top loading, automatic washer and dryer.

The following examples are set forth for purposes of illustration only and are not to be construed as limitations of the present invention except as set forth in the appended claims. All parts and percentages are by weight unless otherwise specified.

EXAMPLE 1

Preparation of

A solution of 1,3-bis(dimethylphosphonomethyl) urea (30.43, 0.1 mole) in 200 ml of distilled water was placed in a 500 ml round-bottomed, three-necked flask, fitted with reflux condenser, thermometer, thermowatch, magnetic stirring bar and stirrer. The solution was adjusted to a pH of 1, with oxalic acid.2H$_2$O, and maintained by heating at 80° C for 8 hours. Heating was discontinued and the flask contents stripped of water solvent in a rotary evaporator (60° C at 20 mm Hg). Purification: The above residue was dissolved in 200 ml of methanol and the resultant solution treated with methanolic sodium hydroxide to a pH of 9, whereupon the tetrasodium salt of 1,3-bis(dihydrophosphonomethyl) urea separated as a grainy solid. The salt was filtered, washed with several portions of cold methanol, followed by dissolution in 200 ml of distilled water and treatment with 60 ml concentrated HCl (aqueous). The aqueous component was stripped exhaustively by a rotary evaporator (50° C at 20 mm of Hg) and the residue dissolved in 200 ml of fresh methanol whereupon sodium chloride precipitated. The product was filtered, the methanol filtrate was stripped, and the residue dissolved in 100 ml of distilled water and subsequently stripped again to an amber oil. On standing, the oil solidified to a white waxy solid which analyzes as 1,3-bis(dihydrophosphonomethyl) urea containing 2–3 molecular water units of hydration. Yield: 85%. Structural verification was made by NMR, infrared spectroscopic and combustion analyses.

EXAMPLE 2

Preparation of

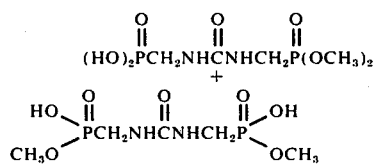

A solution of 1,3-bis(dimethylphosphonomethyl) urea (30.4 g, 0.1 mole) in 200 ml of distilled water was placed in a 500 ml round-bottomed, three-necked flask equipped with thermometer, thermowatch and magnetic stirring bar and stirrer. Oxalic acid was added adjusting the pH to 1 (0.5 gram), and the solution heated to 50° C. The reaction was monitored through NMR analysis of stripped aliquots withdrawn at 30 minute intervals. After 1.5 hours, hydrolysis was 50% complete (based on loss of methoxyl groups). Heat was removed, the flask contents stripped and the residue purified as described in Example 1 above. Twenty-eight grams of product carrying 2 molecular units of water was obtained representing a 90% yield. Structural identification by NMR, infrared spectroscopic and combustion analysis confirmed the structure.

EXAMPLE 3

Preparation of

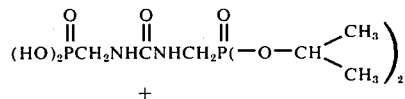

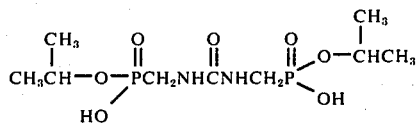

A solution of 1,3-bis(diisopropylphosphonomethyl) urea (100 gram, 0.25 mole) in 300 ml of distilled water was placed in a 1-liter roundbottomed, three-necked flask equipped with a reflux condenser, thermometer, thermowatch and a magnetic stirrer and stirring bar. The pH was adjusted to 1 with oxalic acid and heat was applied through a heating mantle and Variac. Reaction temperature was maintained at 80° C for 3 hours at which time 50% hydrolysis was indicated (NMR was utilized to monitor reaction, aliquots withdrawn at 30 min. intervals). The external heat source was removed, the flask contents were stripped on a rotary evaporator and the residue was purified as described in Example 1. Seventy-five grams (75 g) of product containing 2 molecular units of water was obtained representing an 82% yield.

EXAMPLE 4

Preparation of

A solution of N-(dimethylphosphonomethyl)-methanesulfonamide (50 gram) in 300 ml of distilled water was treated with 1 ml of HCl (conc. aqueous) and refluxed in a 1 liter round-bottomed flask fitted with a reflux condenser, magnetic stirring bar and stirrer, and a heating mantle. NMR monitoring of aliquots withdrawn at 1-day intervals indicated 95% hydrolysis after 4 days. The aqueous product was stripped at 50° C and 20 mm of Hg on a rotary evaporator. The viscous residue was purified as in Example 1. A 75% yield of N-(dihydrophosphonomethyl) methanesulfonamide.3-H$_2$O was obtained. Structure identification by NMR, infrared spectroscopic analysis and combustion data confirmed the structure.

EXAMPLE 5

Preparation of

A solution of N-(dimethylphosphonomethyl) acetamide (18.1 gram) in 200 ml of distilled water was placed in a 500 ml round-bottomed three-necked flask fitted with a reflux condenser, thermometer, thermowatch, magnetic stirring bar and stirrer and a heating mantle with Variac control. The flask contents were adjusted to a pH of 1 with oxalic acid and then maintained at 60° C for 2 days. The aqueous product solution was stripped on a rotary evaporator and the residue subjected to the purification procedure described in Example 1. An 83% yield of N-(dihydrophosphonomethyl) acetamide containing 2–3 molecular units of water was realized. Structure verification by NMR and infrared spectroscopic analysis confirmed the structure.

EXAMPLE 6

Preparation of $$CH_3SO_2NHCH_2P\overset{O}{\underset{OH}{\overset{\|}{-}}}OCH_3$$

Using the reactants and procedure as described in EXAMPLE 4, hydrolysis was taken to 50% completion, which required 48 hours reflux. The product was purified according to Example 1. Spectroscopic analysis, NMR and infrared confirmed the structural identity. A 92% yield of product, as the dihydrate, was obtained.

EXAMPLE 7

Preparation of $$CH_3\overset{O}{\overset{\|}{C}}NHCH_2\overset{O}{\overset{\|}{P}}\overset{OCH_3}{\underset{OH}{}}$$

Using the reactants and procedure as described in Example 5, a 16-hour heating at 60° C gave a 50% hydrolysis product. The product was isolated and purified as described in Example 1. NMR and infrared spectroscopy were used in structure determination. Product containing 2–3 molecular units of water was obtained in 86% yield.

EXAMPLE 8

Preparation of $$\text{C}_6\text{H}_5-\overset{O}{\overset{\|}{C}}NHCH_2\overset{O}{\overset{\|}{P}}(OH)_2$$

A suspension of 1,3-bis(dimethylphosphonomethyl) benzamide 20.1 gram, 0.1 mole) in 200 ml of distilled water was placed in a 500 ml round-bottomed flask equipped with a reflux condenser, stirring bar with stirrer and heating mantle with Variac. Heat was applied, taking the flask contents to reflux. After 3 days, NMR analysis indicated 95% hydrolysis. The product solution was stripped and the residue purified according to the procedure described in Example 1. Spectroscopic analysis by NMR and infrared confirmed the structure of product.

EXAMPLE 9

Sequestering ability and efficiencies for the compounds contained in the invention were determined by titrimetric analysis of solutions containing $Fe^{3+}$, $Cu^{2+}$ and $Ca^{2+}$: The following procedures were used in the determinations.

1. $Fe^{3+}$ 0.5 molar $FeCl_3$ solution was titrated drop-wise into 50 grams of a stirred solution of a given pH containing 0.5 gram of sequestrant. Titration was continued along with simultaneous pH adjustment until a perceptible, permanent haze existed in the solution (end point). The observation of haze is facilitated by passing a light beam through the solution.

Sequestering ability in terms of number of pounds of $Fe^{3+}$ sequestered per 100 pounds of sequestering agent was calculated by multiplying the sequestering efficiency (S.E.) by a factor of 7.1.

2. $Cu^{2+}$

A 0.5 molar $CuCl_2$ solution was titrated drop-wise into 100 grams of a stirred solution at a given pH containing 50 milligrams of potential sequestrant (0.05%). Titration was continued with pH adjustment, until a perceptible, permanent haze prevailed in solution.

Sequestering ability in number of pounds of $Cu^{2+}$ sequestered per 100 pounds of sequestering agent was calculated by multiplying the sequestering efficiency (S.E.) by a factor of 22.0.

3. $Ca^{2+}$

A 0.05 molar $CaCl_2$ solution was titrated drop-wise into 100 grams of a stirred solution at a given pH containing 50 milligrams of sequestrant (0.05%), along with 100 milligrams of sodium carbonate (0.1%) to act as an end-point detector. Titration, with pH adjustment, was continued until a perceptible, permanent haze existed in solution.

Sequestering ability in number of pounds of $Ca^{2+}$ sequestered per 100 pounds of sequestering agent was calculated by multiplying the sequestering efficiency (S.E.) by a factor of 10.1.

Results of representative compounds and their sequestering activity are tabulated in Table I.

TABLE I

| | Sequestering Efficiencies | | | | | | | | | | | | | | |
|---|---|---|---|---|---|---|---|---|---|---|---|---|---|---|---|
| | $Fe^{3+}$ | | | | | $Cu^{2+}$ | | | | | $Ca^{2+}$ | | | | |
| Compound | pH 4 | pH 6 | pH 8 | pH 10 | pH 12 | pH 4 | pH 6 | pH 8 | pH 10 | pH 12 | pH 4 | pH 6 | pH 8 | pH 10 | pH 12 |
| 1,3-bis(dihydrophosphonomethyl) urea | .04 | .08 | .10 | .50 | .04 | 14+ | 80 | 20 | .10 | .07 | 19+ | 19+ | 19+ | 3.4 | 2.1 |
| $HO\underset{HO}{\overset{}{>}}\overset{O}{\overset{\|}{P}}CH_2NH\overset{O}{\overset{\|}{C}}NHCH_2\overset{O}{\overset{\|}{P}}\underset{OCH_3}{\overset{OCH_3}{<}}$ | | | | | | | | | | | | | | | |

TABLE I-continued

| Compound | Sequestering Efficiencies | | | | | | | | | | | | | | |
|---|---|---|---|---|---|---|---|---|---|---|---|---|---|---|---|
| | $Fe^{3+}$ | | | | | $Cu^{2+}$ | | | | | $Ca^{2+}$ | | | | |
| | pH 4 | pH 6 | pH 8 | pH 10 | pH 12 | pH 4 | pH 6 | pH 8 | pH 10 | pH 12 | pH 4 | pH 6 | pH 8 | pH 10 | pH 12 |
| $HO-\overset{O}{\underset{\|}{P}}CH_2NHCNHCH_2\overset{O}{\underset{\|}{P}}-OCH_3$ (with $CH_3O$ and $OH$ groups) + | .06 | .08 | .10 | .42 | .08 | 6+ | 1.0 | .40 | .32 | .25 | 12+ | 12+ | 12+ | 3.9 | 1.82 |
| $HO-\overset{O}{\underset{\|}{P}}CH_2NHCNHCH_2\overset{O}{\underset{\|}{P}}-O-CH(CH_3)_2$ (bis-isopropyl) + | .08 | .12 | .12 | .83 | .24 | 6+ | 1.01 | .51 | .51 | .51 | 12+ | 12+ | 8+ | 4.05 | 1.51 |
| (mixed methyl/isopropyl phosphonomethyl urea) | | | | | | | | | | | | | | | |
| N-(dihydrophosphono-methyl) methanesulfon-amide | .80 | .60 | .30 | .08 | .08 | 14+ | 1.1 | .50 | .20 | .10 | 19+ | 19+ | 19+ | 2.8 | 1.3 |
| N-(dihydrophosphono-methyl) acetamide | .63 | .51 | .47 | .39 | .16 | 3+ | 0.98 | .64 | .53 | .22 | 12+ | 12+ | 12+ | 1.39 | .01 |

EXAMPLE 10

A padding solution was prepared containing 50 parts of 1,3-bis(dihydrophosphonomethyl) urea, 49.5 parts water, and 0.5 part Triton X-100 wetting agent.

5.0 oz. per sq. yard cotton sheeting was then padded through the solution and squeezed to about 95% wet pick-up on a two roll laboratory padder at 60 lb./in.$^2$ gauge pressure. The sheeting was then dried for about 2.5 minutes at about 200° F. and cured for about 2 minutes at about 360° F in a circulating air oven. The sheeting was then scoured in an automatic washer with 10 g. of Tide detergent, 50 g. of soda ash, 50 g. of sodium perborate and water (13 gal.), tumbled dry, decreasing the weight add-on to about 18.5%. The thus treated sheeting was subjected to AATCC Test 34-1969 and had a char length of 2.125 inches. The oxygen index of the treated sheeting was 32. The treated sheeting was subjected to 10 home washes with 50 gr. of Tide and ½ cup of Calgon water softener in each. The thus washed, treated sheeting had a char length of 1¼ inches when subjected to the AATCC Test 34-1969 and an oxygen index of 32 when subjected to the oxygen index test.

EXAMPLE 11

58 parts of partially hydrolyzed 1,3-bis(diisopropyl phosphonomethyl) urea was made into a pad solution with 41.5 parts water and 0.5 parts Triton X-100 wetting agent.

5.0 oz. per sq. yard cotton sheeting was then padded through the solution and squeezed to about 94.7% wet pick-up on a two roll laboratory padder. After drying at about 200° F for about 2½ minutes, the sheeting was cured at about 360° F for about 5 minutes. The thus treated sheet was scoured and dried as described in Example 10, the treated sheeting showed a decrease of weight add-on to 13.5%, and an oxygen index of 30. Untreated cotton sheeting had an oxygen index of 20.

EXAMPLE 12

50 parts of N-(dihydrophosphonomethyl) acetamide was mixed with 49.9 parts water and 0.1 part Triton X-100 into a pad solution.

5.0 oz. per sq. yard cotton sheeting was padded through the solution and squeezed to about 90% wet pick-up on the two roll laboratory padder. After drying at about 200° F for about 2.5 minutes and curing at about 360° F for about 2 minutes, the treated sheeting was scoured and dried as described in Example 10, showing a 14.7% weight add-on after drying. When tested by the AATCC Test 34-1969 method, the char length was 1.75 inches. The oxygen index of the treated sheeting was 32.

EXAMPLE 13

A solution containing 40 parts N-(dihydrophosphonomethyl) methane sulfonamide, 59.9 parts water, and 0.1 parts Triton X-100 wetting agent was prepared.

5.0 oz. per sq. yard cotton sheeting was padded through the solution and showed a wet pick-up of about 92.0% after being squeezed through the two-roll laboratory padder at 60 lbs./in$^2$ gauge pressure. The wet padded sheeting was dried at about 200° F for about 2.5 minutes, cured at 360° F for about 3 minutes, scoured and dried as described in Example 10. The thus treated sheeting showed a weight add-on of about 13.8%, a char length of 2.25 inches when tested by the AATCC Test 34-1969 method, and an oxygen index of 32.

EXAMPLE 14

40.8 parts of partially hydrolyzed, 1,3-bis(dimethylphosphonomethyl) urea was mixed with 58.7 parts water and 0.5 parts Triton X-100 wetting agent.

5.0 oz. per sq. yard cotton sheeting was padded through the solution and squeezed to about 94.9% wet pick-up on the two roll laboratory padder at 60 lb./in$^2$ gauge pressure. The sheeting was then dried for about 2.5 minutes at about 200° F and cured 10 minutes at about 320° F in a circulating air oven. The treated sheeting was then scoured in an automatic washer by the method of Example 10, dried and showed a weight add-on of 11.5%. The treated sheeting had a char length of 1¼ inches when tested by the AATCC Test 34-1969 and an oxygen index of 32.

We claim:

1. A process for sequestering metal ions comprising treating said ions with about 0.001 to about 50 percent aqueous solution of a compound of the formula:

$$\begin{array}{c}R'\\ \diagdown\\ R'\end{array}\!\!\overset{O}{\underset{\|}{P}}CH_2NH\overset{O}{\underset{\|}{C}}NHCH_2\overset{O}{\underset{\|}{P}}\!\!\begin{array}{c}OH\\ \diagup\\ R'\end{array}$$

wherein R' is selected from the group consisting of ⁻OH, alkyloxy and aryloxy.

2. The process of claim 1 wherein said metal ions are cations having a valence of two or more.

3. The process of claim 1 wherein said metal ions are selected from the group consisting of calcium, chromium, copper, nickel, tin, iron, aluminum, cobalt, platinum, palladium, rhodium, iridium, ruthenium, osmium, zirconium, hafnium, the rare earths and the actimides.

4. The process of claim 1 wherein said compound is added in solution to the metal ions to be sequestered.

5. The process of claim 1 wherein said concentration is from about 0.01 to about 5 percent by weight.

6. The process of claim 1 wherein said concentration is from about 0.1 to about 3 percent by weight.

7. The process of claim 1 wherein the process is maintained at a temperature from about 0° to about 100° centigrade.

8. The process of claim 7 wherein said temperature is from about 20° to about 70° centigrade.

9. A process of claim 1 wherein R' is OH.

10. The process of claim 1 wherein R' is alkoxy of 1–6 carbon atoms.

11. The process of claim 1 wherein at least one R' is an alkyloxy moiety of 1–6 carbon atoms.

12. The process of claim 1 wherein the compound is $$(HO)_2\overset{O}{\underset{\|}{P}}CH_2NH\overset{O}{\underset{\|}{C}}NHCH_2\overset{O}{\underset{\|}{P}}(OH)_2.$$

13. The process of claim 1 wherein the compound is $$(HO)_2\overset{O}{\underset{\|}{P}}CH_2NH\overset{O}{\underset{\|}{C}}NHCH_2\overset{O}{\underset{\|}{P}}(OCH_3)_2.$$

14. The process of claim 1 wherein the compound is $$\begin{array}{c}HO\\ \diagdown\\ CH_3O\end{array}\!\!\overset{O}{\underset{\|}{P}}CH_2NH\overset{O}{\underset{\|}{C}}NHCH_2\overset{O}{\underset{\|}{P}}\!\!\begin{array}{c}OH\\ \diagup\\ OCH_3\end{array}.$$

15. The process of claim 1 wherein the compound is $$(HO)_2\overset{O}{\underset{\|}{P}}CH_2NH\overset{O}{\underset{\|}{C}}NHCH_2\overset{O}{\underset{\|}{P}}\!\!\left(\!-O-CH\!\!\begin{array}{c}CH_3\\ \diagup\\ \diagdown\\ CH_3\end{array}\!\right)_{\!2}.$$

16. The process of claim 1 wherein the compound is $$\begin{array}{c}CH_3\\ |\\ CH_3CH-O-\end{array}\!\!\overset{O}{\underset{|}{\underset{HO}{P}}}CH_2NH\overset{O}{\underset{\|}{C}}NHCH_2\overset{O}{\underset{\|}{P}}\!\!\begin{array}{c}CH_3\\ |\\ O-CHCH_3\\ \diagdown\\ OH\end{array}.$$

17. The process of claim 1 wherein at least one R' is a halogenated aryloxy moiety.

* * * * *

UNITED STATES PATENT OFFICE
CERTIFICATE OF CORRECTION

PATENT NO. : 3,992,294
DATED : November 16, 1976
INVENTOR(S) : Daniel J. Scharf and Howard A. Chamberlin It is certified that error appears in the above—identified patent and that said Letters Patent are hereby corrected as shown below:

Column 1, line 38 "as wel as" should read --as well as--.
Column 14, Table 1

" $\dfrac{Cu^{2+}}{pH_4 \ pH_6 \ pH_8 \ pH_{10} \ pH_{12}}$ " should read -- $\dfrac{Cu^{2+}}{pH_4 \ pH_6 \ pH_8 \ pH_{10} \ pH_{12}}$ --
14+ 80   20   .10   .07                              14+ .80  .20  .10   .07

Signed and Sealed this

*Twenty-seventh* Day of *September 1977*

[SEAL]

Attest:

RUTH C. MASON
*Attesting Officer*

LUTRELLE F. PARKER
*Acting Commissioner of Patents and Trademarks*